United States Patent [19]
Kiesele et al.

[11] Patent Number: 5,372,696
[45] Date of Patent: Dec. 13, 1994

[54] ELECTROCHEMICAL SENSOR OF MODULAR DESIGN

[75] Inventors: Herbert Kiesele, Lübeck; Uwe Kühn, Wesenberg, both of Germany

[73] Assignee: Drägerwerk AG, Lubeck, Germany

[21] Appl. No.: 93,784

[22] Filed: Jul. 19, 1993

[30] Foreign Application Priority Data

Sep. 12, 1992 [DE] Germany .................... 4230602

[51] Int. Cl.$^5$ ............................................ G01N 27/26
[52] U.S. Cl. ................................. 204/416; 204/415; 204/412; 204/431; 204/432
[58] Field of Search ............... 204/416, 412, 415, 400, 204/267, 253, 431, 432; 422/82.03, 82.04

[56] References Cited

U.S. PATENT DOCUMENTS

4,474,648 10/1984 Tantram .................... 204/415
4,797,192 1/1989 Takaguchi .................... 204/416

*Primary Examiner*—Kathryn Gorgos
*Assistant Examiner*—Bruce F. Bell
*Attorney, Agent, or Firm*—McGlew and Tuttle

[57] ABSTRACT

An electrochemical sensor for fluid media with at least two electrodes, which are in contact with one another via an electrolyte and are accommodated in a housing. Many different sensor variants are attainable with a few, standardized components. The housing (1) includes a plurality of modules (4a, 4b; 4c–4m), which are placed next to one another, are designed as hollow bodies, and are connected to one another, wherein at least two lateral surfaces (9) of each module (4a–4m) are suitable for connection to additional modules (4a–4m), and at least two of the modules (4a, 4b; 4c–4m) accommodate one electrode (2, 3) each, and the hollow space (16) enclosed by the modules (4a, 4b; 4c–4m) is delimited from the environment by the two electrodes (2, 3), on the one hand, and by a partial area (17) each of the inner wall (5) of the modules (4a, 4b; 4c–4m), and is provided for accommodating the electrolyte (18).

20 Claims, 7 Drawing Sheets

ELECTROCHEMICAL SENSOR OF MODULAR DESIGN

FIELD OF THE INVENTION

The present invention pertains to an electrochemical sensor for fluid media with at least two electrodes, which are in contact with one another via an electrolyte and are accommodated in a housing.

BACKGROUND OF THE INVENTION

Electrochemical sensors are used for various types of measuring tasks, such as leak detection, the monitoring of maximum allowable concentrations, and process monitoring, and a large number of gases and vapors, as well as various concentration ranges must be covered. In addition, the sensors are integrated in both portable and stationary devices. This means that a plurality of sensor lines with different geometries are needed, and a broad spectrum of individual sensors must be made available within one line for different species and different concentration ranges.

The components of such sensors are usually installed in a line-specific housing (e.g., U.S. Pat. No. 4,474,648). This leads to high costs in design, manufacture, and storage. If a new sensor is to be made, e.g., with another electrode arrangement or another electrolyte volume, it is necessary to newly design a housing that is suitable for it.

SUMMARY AND OBJECTS OF THE INVENTION

The object of the present invention is to propose a sensor, whose design can be adapted to the actual requirements, without the need to design or manufacture a specially adapted housing.

This object is attained by the housing being composed of a plurality of modules, which are attached to one another, are designed as hollow bodies, and are connected to one another, wherein at least two lateral surfaces on each module are suitable for connection to additional modules, and at least two of the modules have an electrode each, and the hollow space enclosed by the modules is delimited from the environment by the two electrodes, on the one hand, and by a partial area each of the inner wall of the modules, and is provided for accommodating the electrolyte.

The advantage of the present invention is that a housing can be made from a few standardized modules for each desired sensor. The costs of design, manufacture, and storage decrease considerably compared with a design with specially adapted housings, because the modules, assembled depending on the particular needs, now form the housing itself. Modules of identical geometric shape are preferably used. This means at least that at the points at which two modules are connected the modules are of identical design or of such a design that they can be assembled. The shape and the size of the modules may be different from one module to the next. However, only two or three different modules are combined with one another in order to fully utilize the advantage of building various sensors with a few standard components. All these modules are now preferably of, e.g., cylindrical design, and all have identical design at the surfaces at which they are connected to one another.

By using more than two modules, it is possible to prepare, e.g., sensors with three electrodes and/or sensors with increased electrolyte reserve. The electrolyte reserve can be further increased when modules with enlarged volume are combined with the standard modules. The connection points of all modules are of identical design, so that any random combination of the modules is guaranteed.

It is also possible to use modules which have, e.g., at one front surface, two or three connection points arranged next to one another for other modules. It is thus possible to prepare sensors with many electrodes (e.g., a multigas sensor).

Furthermore, a module or even a plurality of modules of a sensor may be a tetrahedron, cube, parallelepiped, or another polyhedron. Several or even all lateral surfaces may be provided for connection to other modules. A sensor may be composed of, e.g., a cube-shaped module used as the electrolyte reserve and up to six (cylindrical) modules with built-in electrodes attached to it.

The modules may be connected to one another by screwing, bonding, or welding. Front surfaces of corresponding shape, by which the modules touch each other, and which fix the modules radially and possibly even axially in their mutual positions (e.g., snap-in devices), may be used as mounting aids. The front surfaces may be coupled with one another directly or via adapters.

If a snap-in device is used, which permits liquid-tight connection of the modules, e.g., by the use of a seal, additional bonding or welding may be omitted.

Dogs, edges, or other projections, which are used to accommodate sensor components, such as electrodes, membranes, bottom plates, and diffusion diaphragms, may be arranged inside the modules.

The various features of novelty which characterize tile invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
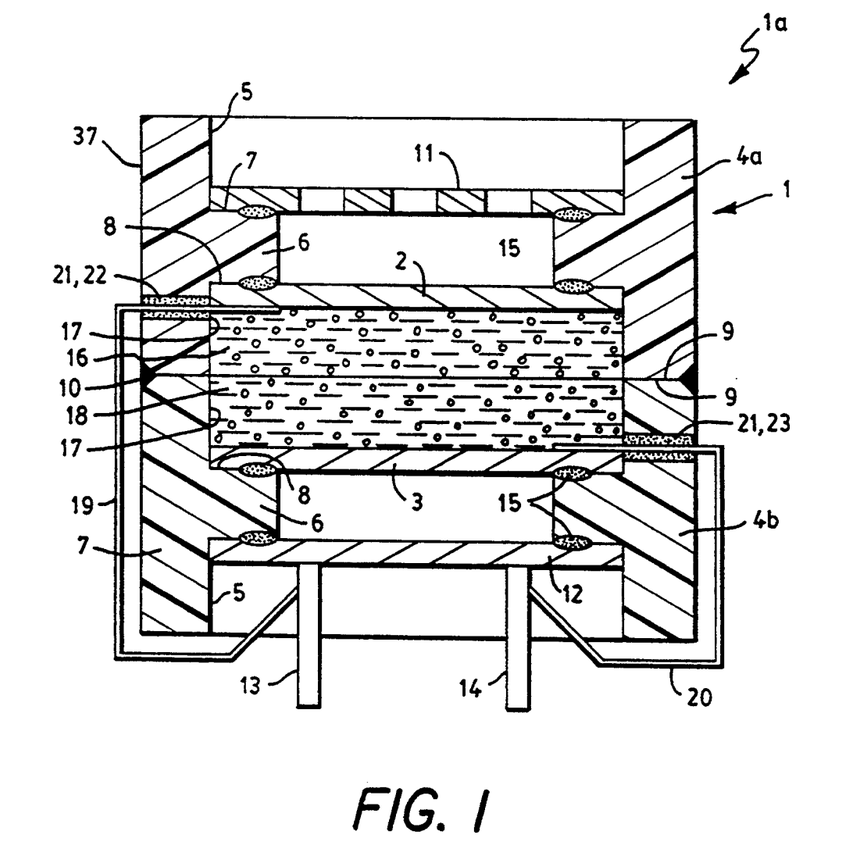
FIG. 1 is a sectional view showing a sensor with two electrodes.

FIG. 1 shows a gas sensor $1a$ with a working electrode 2 and a counterelectrode 3. The electrodes 2, 3 are accommodated in a module $4a$, $4b$ each. Both the modules $4a$, $4b$ form together a housing 1 for the gas sensor $1a$. The modules $4a$, $4b$ are identical in terms of their geometric shape. These are essentially tubular sections with cylindrical outer wall 37 made of, e.g., a thermoplastic, which have a bead 6 on their inner wall 5. The two front sides of the bead 6 form a holding edge 7, 8 each for accommodating sensor component.

The two modules 4a, 4b are mounted centrally relative to one another with one of their front surfaces 9 each, and are connected to one another by a weld seam 10.

The holding edge 7 of the module 4a, which edge is located on the outside, carries a diffusion diaphragm 11, which regulates the access of the gas to be measured to the sensor 1a. The holding edge 8, which is located on the inside, carries the working electrode 2. The holding edge 8 of the other module 4b, which edge is located on the inside, carries the counterelectrode 3, and the holding edge 7, which is located on the outside, carries a mounting plate 12 with contact pins 13, 14. The diffusion diaphragm 11, electrodes 2, 3, and mounting plate 12 are fastened to the respective holding edge 7, 8 with adhesive 15 or a weld seam.

The hollow space 16 within the two modules 4a, 4b, which is delimited by the two electrodes 2, 3 and one partial area 17 of each of the inner walls 5 (a portion of each inner wall 5 delimits hollow space 16) of the modules 4a, 4b, is filled with an electrolyte 18.

The electrodes 2, 3 are connected to the contact pins 13, 14 by contact wires 19, 20. The contact wires 19, 20 are led out of the hollow space 16 through housing holes 22, 23 sealed with adhesive 21.

Figure 2:
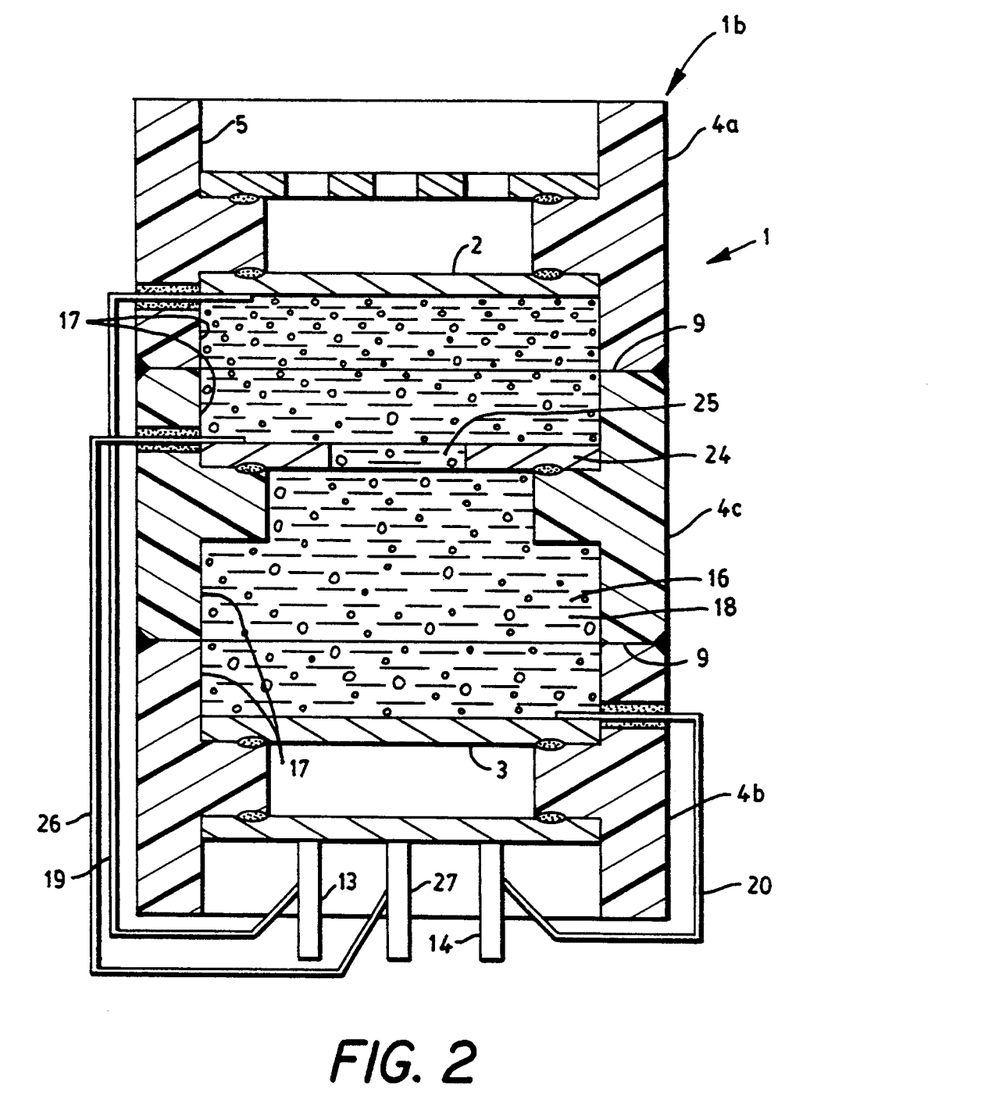
FIG. 2 is a sectional view showing a sensor with three electrodes.

The sensor 1b shown in FIG. 2 has a third module 4c between the two modules 4a, 4b (FIG. 1). The design is otherwise identical to that of the sensor 1a shown in FIG. 1. The third module 4c carries a reference electrode 24, which is provided with a hole 25, through which the electrolyte 18 can come into contact with all the electrodes 2, 3, 24. The reference electrode 24 is connected to a third contact pin 27 by a contact wire 26.

Figure 3:
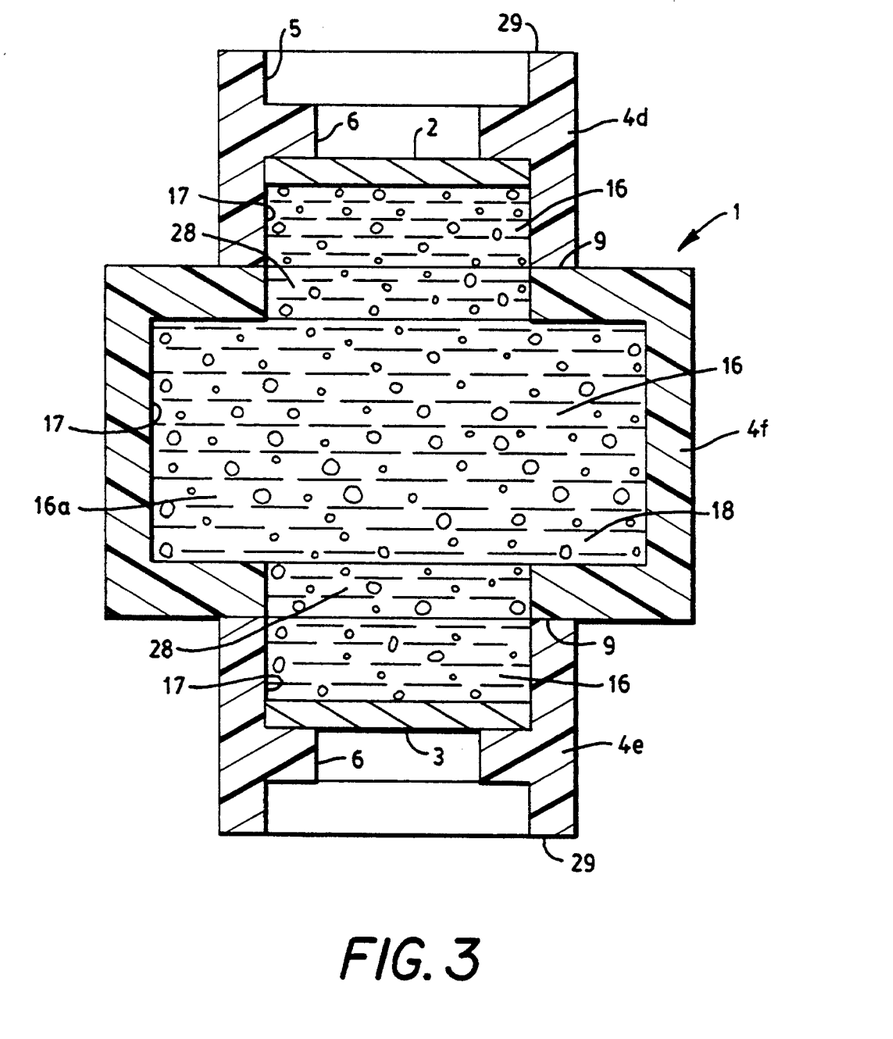
FIG. 3 is a sectional view showing modules of various sizes, combined in a housing.

FIG. 3 shows a housing 1 of a sensor with two electrodes 2, 3. It consists of two identical modules 4d, 4e and a larger module 4f, which is arranged between these and has an enlarged hollow space 16a. On its front surfaces 9, the intermediate module 4f has openings 28, via which the hollow spaces of the modules 4d, 4e, 4f are connected to an overall hollow space 16. The modules 4d, 4e are longer than the modules 4a-4c according to FIGS. 1 and 2, and the bead 6 is not arranged centrally, but is displaced toward the outer end 29 of the each module. This displacement and the central module 4f lead to a greatly enlarged hollow space 16 for accommodating the electrolyte 18 compared with the designs according to FIGS. 1 and 2.

FIGS. 4a–4d show schematically how many different housing variants can be obtained with only two modules 4g, 4h of different size, which can be combined with one another on their front surfaces 9.

Figure 4A:
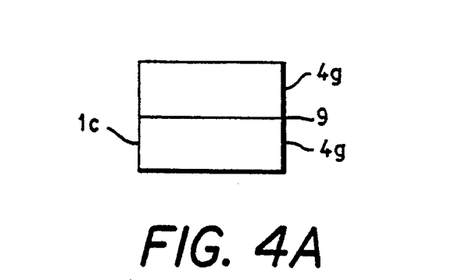
FIGS. 4a–4d are schematic views showing various combinations of modules.
Figure 4B:
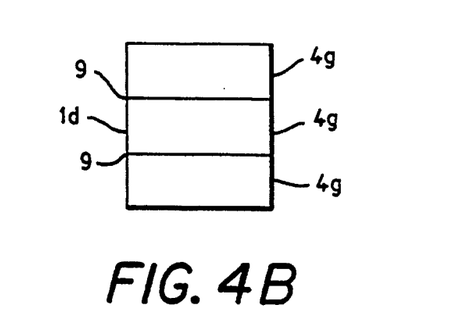

FIG. 4a shows two small modules 4g, combined into a sensor 1c with two electrodes (corresponding to FIG. 1). FIG. 4b shows three small modules 4g, combined into a sensor 1d with three electrodes (corresponding to FIG. 2).

However, FIG. 4b may also represent a sensor 1d with two electrodes with increased electrolyte reserve. The central module 4g contains no electrode in this case.

Figure 4C:
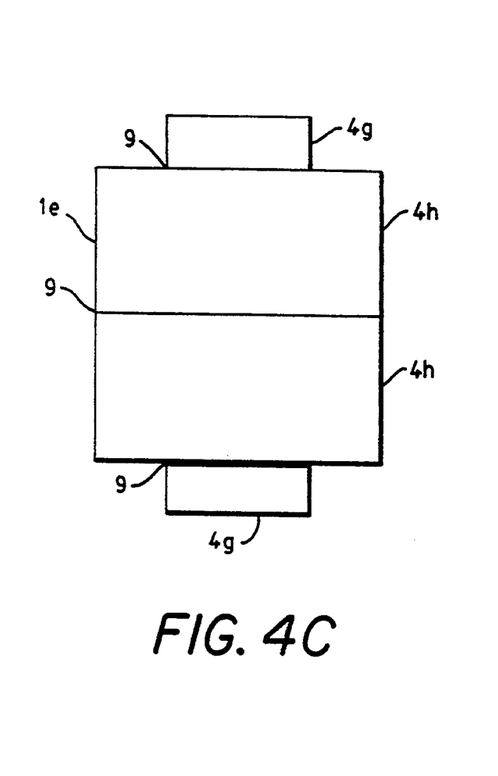

FIG. 4c shows a sensor 1e with two electrodes, which are arranged in the terminal small modules 4g. Two large modules 4h, which are used to greatly increase the electrolyte reserve, are arranged between the modules 4g.

Figure 4D:
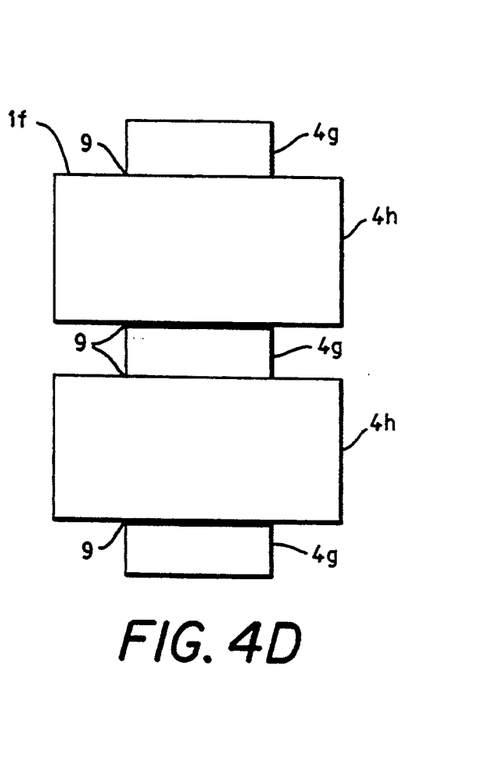

FIG. 4d shows a sensor 1f with three electrodes, which are arranged in the small modules 4g. One large module 4h is arranged between two of the small modules 4g each to increase the electrolyte reserve.

Figure 5A:
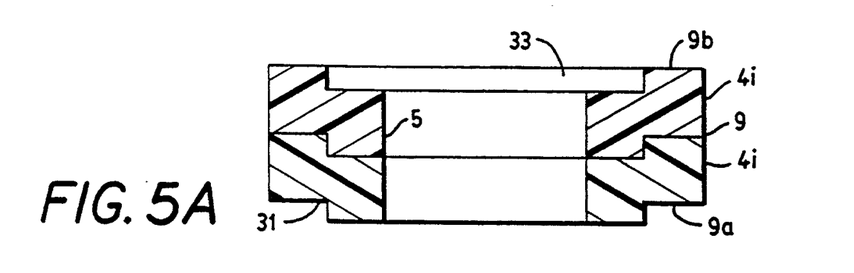
FIGS. 5a–5e are various embodiments of front surface contours of the modules.

FIGS. 5a–5e show various embodiments of the front surface contours of the modules. FIG. 5a shows two modules 4i placed one inside the other. Each module 4i carries a positive contour in the form of a shoulder 31 on the front surface 9a and a negative contour in the form of a recess 33, which can be assembled with the positive contour 31, on the opposite front surface 9b. As a result, the two modules are secured against radial displacement, which considerably facilitates their installation. For example, a device, which accommodates the modules during their welding into a finished sensor, can have a considerably simpler design.

Figure 5B:
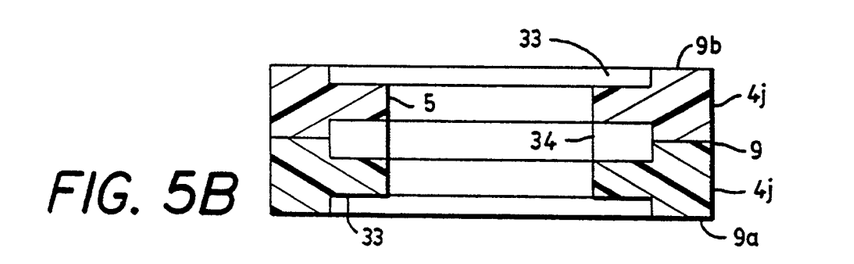

FIG. 5b shows modules 4j, which have the negative contours 33 on both the front surfaces 9a, 9b. The positive contour needed for assembling is formed by a connection piece in the form of a ring 34.

Figure 5C:
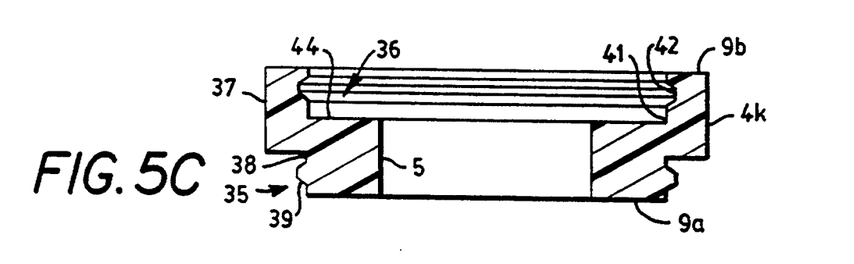
Figure 5D:
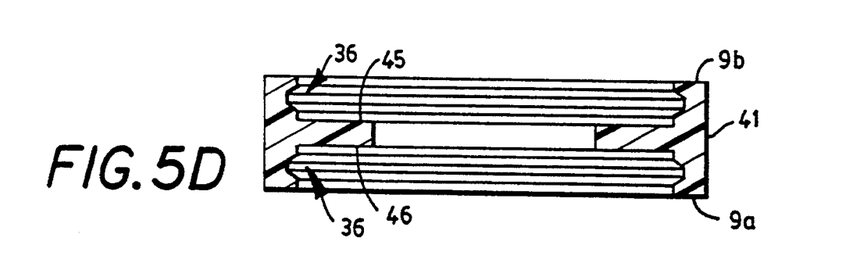

FIGS. 5c and 5d show modules 4k, 4l with snap-in connections, which secure against radial and axial displacements. The assembly of modules into a sensor can thus be performed very easily.

FIG. 5c shows a module 4k, which has, analogously to tile module 4i according to FIG. 5a, a positive contour 35 on one front surface 9a and a fitting negative contour 36 oil tile other front surface 9b.

In the area of tile positive contour 35, the external diameter of the module 4k is reduced compared with the rest of the area 37 of the cylindrical outer wall, so that a shoulder 38 is obtained. A circumferential collar 39 of trapezoidal cross section is arranged on the shoulder 38.

The internal diameter of the module 4k is increased in the area of the negative contour 36 compared with the rest of the area 5, so that a recess 41 is obtained. A circumferential groove 42 of trapezoidal cross section is arranged in the recess 41.

The positive contour 35 of one the module 4k can be snapped into the negative contour 36 of another module 4k by axial pressure.

FIG. 5d shows a module 4l which has the negative contours 36 on both the front surfaces 9a, 9b. An annular connection piece 43, which has two positive contours 35 arranged next to each other, is used to connect two modules 4l.

Inner front surfaces of the modules 4k, 4l are used as holding edges 44, 45, 46 for arranging sensor components.

Figure 5E:
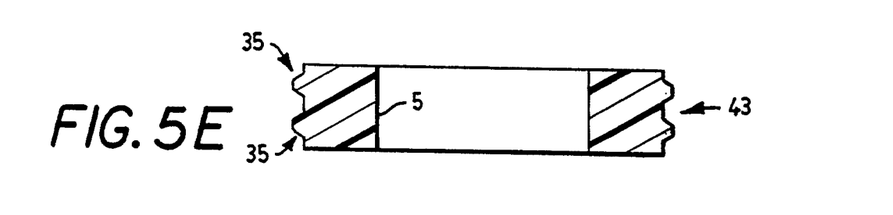
Figure 6:
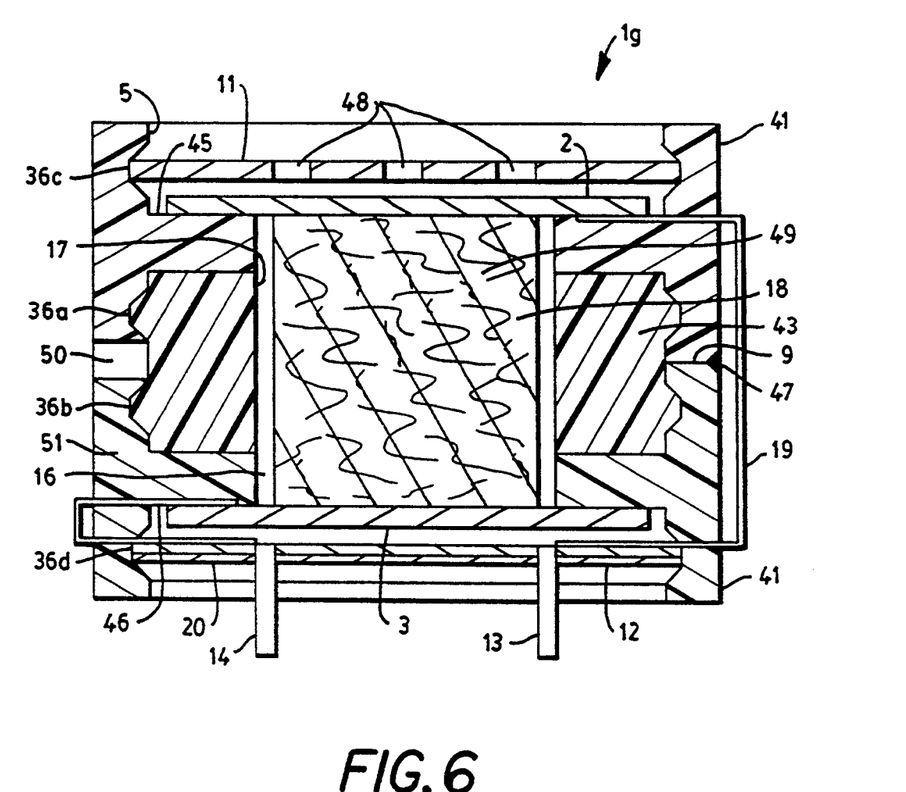
FIG. 6 is a sectional view showing a sensor with two electrodes and a pressure-equalizing hole.

FIG. 6 shows a sensor 1g, which is composed of two modules 4l and a connection piece 43 corresponding to FIGS. 5d and 5e. The two modules 4l are connected by a weld seam 47 in a liquid-tight manner. The connection piece 43 is snapped into the two inner negative contours 36a, 36b. A diffusion diaphragm 11 is snapped into the outer negative contour 36c. This diffusion diaphragm 11 has a plurality of holes 48, through which, e.g., gas, has access to the sensor 1g from the environment. A mounting plate 12 is snapped into the outer negative contour 36d. The electrodes 2, 3 are attached to the two holding edges 45, 46 of the modules 4l. The electrodes 2, 3 are connected via the contact wires 19, 20 to the contact pins 13, 14 on the mounting plate 12 (as was described in connection with FIG. 1). A cylindrical piece of glass fiber mat 49, which extends from the working electrode 2 to the counterelectrode 3 and is impregnated with the electrolyte 18, is arranged in the hollow space 16 of the sensor 1g.

To ensure pressure equalization between the hollow space 16 and the environment under varying conditions of use of the sensor 1g, a pressure-equalizing hole 50 is provided in the wall 51 at one point on the circumference of the sensor 1g in the area of tile weld seam 47. To prevent the electrolyte 18 from escaping through the hole 50, the connection piece 43 is dimensioned such that it is in sealing contact with the modules 41. To make it possible for gas to escape through the pressure-equalizing hole 50, the connection piece 43 is made of a porous plastic (e.g., PTFE).

Figure 7:
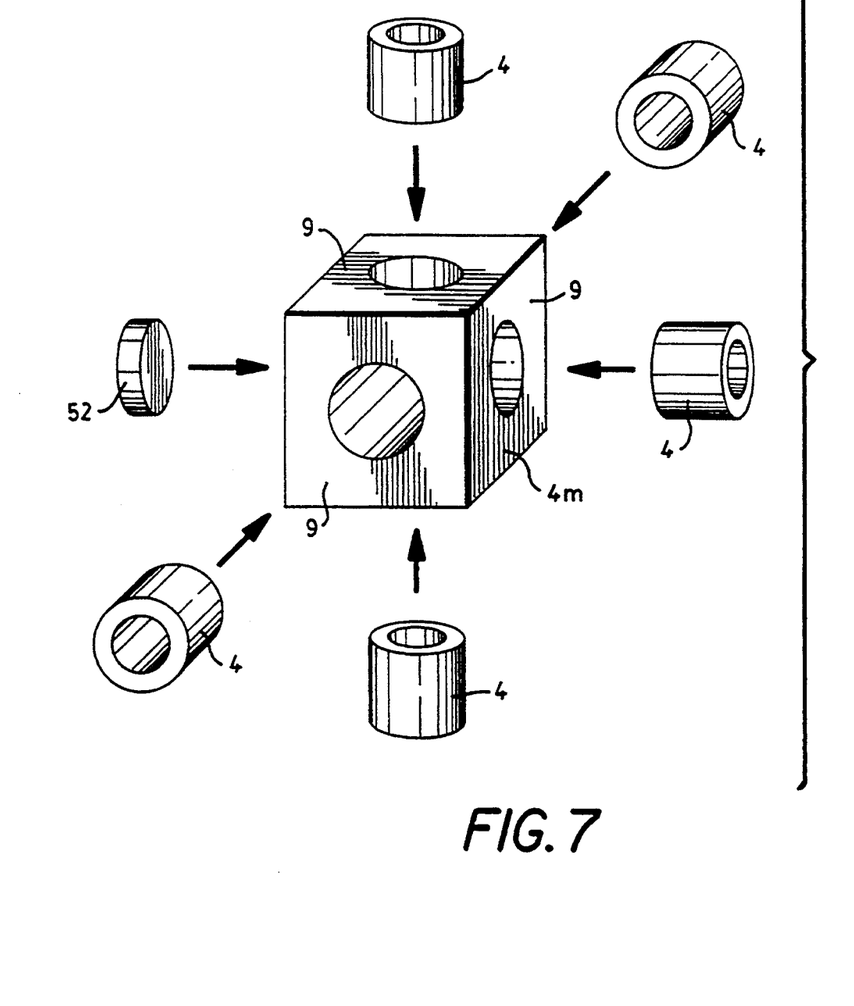
FIG. 7 is a sectional view showing a sensor with a cube-shaped module.

FIG. 7 shows a cube-shaped module 4m, whose six lateral surfaces 9 are suitable for connection to additional modules 4. Lateral surfaces 9 that are not needed may be made as closed lateral surfaces, or they may be closed with a plug 52. The lateral surfaces 9 may be provided with one of the front surface contours shown in FIG. 5 (not specifically shown in FIG. 7). The cube-shaped module 4m is used as an electrolyte reserve in this case, and the coupled modules 4 carry an electrode each. It is thus possible to prepare a sensor for the simultaneous measurement of a plurality of substances.

One or two of the embodiments of the modules 4a–4m shown are preferably selected. For example, two modules of different size e.g., 4g, 4h are provided with uniform front surface contours (e.g., as in FIG. 6), and a modular system is thus available, with which many different sensors can be prepared.

While specific embodiments of the invention have been shown and described in detail to illustrate the application of the principles of the invention, it will be understood that the invention may be embodied otherwise without departing from such principles.

What is claimed is:

1. Electrochemical sensor for fluid media, comprising:
   a housing formed of a plurality of modules, each of said modules being formed of a hollow body, each module having at least two lateral surfaces forming connection surfaces for connection to another of said plurality of modules to form connected modules;
   two electrodes positioned in said connected modules, each of said electrodes being connected to one of said modules to delimit a connected module combined hollow space, said connected module hollow space further being delimited by a partial area on the inner wall of each of said modules; and
   an electrolyte enclosed within said combined hollow space.

2. A sensor according to claim 1, wherein:
   at least two of said plurality of modules have identical geometric shape.

3. A sensor according to claim 1, wherein:
   modules connected to said electrodes are designed as end modules, an additional module being positioned between said end modules arranged as a central module, said central module carrying another electrode, which is permeable to said electrolyte, said central module having a hollow space in contact with said combined hollow space whereby the hollow space of the three modules is delimited from the environment by two electrodes arranged in said end modules and by a partial area of the inner wall of each of said end modules and said central module, said hollow space of three modules accommodating said electrolyte.

4. A sensor according to claim 1, wherein:
   said modules connected to said electrodes are designed as end modules with one or more intermediate modules being positioned therebetween, said one of more intermediate modules defining an essentially closed hollow space having openings on lateral surfaces facing said end modules, said intermediate modules hollow space and said combined hollow space of said end modules forming an overall hollow space accommodating said electrolyte.

5. A sensor according to claim 3, wherein:
   said central module encloses a hollow space which is larger than a hollow space enclosed by said end modules.

6. A sensor according to claim 4, wherein:
   said intermediate modules enclose a hollow space which is larger than a hollow space enclosed by said end modules.

7. A sensor according to claim 1, wherein:
   each of said plurality of modules are annular with an essentially cylindrical outer wall, each of said modules having a front surface for connection with a front surface of another module.

8. A sensor according to claim 1, wherein:
   the shape of at least one of said modules is tetrahedral, parallelepipedic, or polyhedral.

9. A sensor according to claim 1, wherein:
   a holding edge is provided extending from an inner wall of said modules.

10. A sensor according to claim 1, wherein:
    said modules have a positive contour on a front surface and a negative contour, corresponding to said positive contour on an opposite front surface.

11. A sensor according to claim 1, wherein:
    said modules have identical negative contours on each of a first front surface and a second front surface, a connection piece being provided for connecting two modules, said connection piece including a positive contour corresponding to said negative contour of said modules.

12. A sensor according to claim 10, wherein:
    said positive contour is provided to form a snap-in connection with said negative contour for connection of two modules and securing two modules against radial and axial displacement.

13. A sensor according to claim 12, wherein:
    said positive contour is designed as a collar arranged on a shoulder of one of said modules, said negative contour being designed as a groove arranged in a recess of said module, said recess for accommodating said collar.

14. A sensor according to claim 10, wherein:
    said positive contour and said negative contour are provided for accommodating additional sensor components including one of a connection plate and diffusion diaphragm.

15. A sensor according to claim 11, wherein:
    said connection piece is designed as a gas permeable connection piece, in an area adjacent said connection piece, a wall of at least one of said modules having a pressure-equalizing hole extending from said combined hollow space to the environment.

16. Electrochemical sensor for fluid media, comprising:
    a housing formed of a plurality of modules, each of said modules being formed of a hollow body, each module having at least two lateral connection surfaces for connection to another of said plurality of modules to provide connected modules forming said housing;

a first electrode connected to a first one of said connected modules;

a second electrode connected to a second one of said connected modules, said first electrode, said second electrode and a portion of an inner wall of said first connected module and a portion of an inner wall of said second connected module cooperating to delimit an enclosed connected module combined hollow space; and an electrolyte accommodated in said enclosed combined hollow space, with said first electrode having a hollow space facing side in contact with said electrolyte and with said second electrode having a hollow space facing side in contact with said electrolyte.

17. A sensor according to claim 16, further comprising:

a connection piece for connecting two modules, said connection piece including two connection surfaces for connection to connection surfaces of said modules.

18. A sensor according to claim 17, wherein:

said connection piece is designed as a gas permeable connection piece, in an area adjacent said connection piece, a wall of at least one of said modules having a pressure-equalizing hole extending from said combined hollow space to the environment.

19. A sensor according to claim 16, wherein: said modules are of substantially identical design.

20. A sensor according to claim 1, wherein: said modules are of substantially identical design.

* * * * *